United States Patent
Musaeus et al.

(10) Patent No.: US 10,449,153 B2
(45) Date of Patent: Oct. 22, 2019

(54) PROCESS FOR PRODUCING A PREPARATION IN POWDER FORM CONTAINING AT LEAST ONE CAROTENOID

(71) Applicant: BASF SE, Ludwigshafen (DE)

(72) Inventors: Nina Musaeus, Hellerup (DK); Carsten Ninn Jensen, Roedovre (DK)

(73) Assignee: BASF SE (DE)

( * ) Notice: Subject to any disclaimer, the term of this patent is extended or adjusted under 35 U.S.C. 154(b) by 0 days.

(21) Appl. No.: 15/145,373

(22) Filed: May 3, 2016

(65) Prior Publication Data

US 2016/0338964 A1 Nov. 24, 2016

Related U.S. Application Data

(62) Division of application No. 11/994,022, filed as application No. PCT/EP2006/063627 on Jun. 28, 2006, now Pat. No. 9,357,796.

(30) Foreign Application Priority Data

Jun. 30, 2005 (DE) .................. 10 2005 030 952

(51) Int. Cl.
| | |
|---|---|
| *A61K 31/015* | (2006.01) |
| *A61K 47/26* | (2006.01) |
| *A61K 9/16* | (2006.01) |
| *C09B 61/00* | (2006.01) |
| *C07C 403/24* | (2006.01) |
| *A61K 31/07* | (2006.01) |
| *A23L 5/44* | (2016.01) |
| *A23L 33/105* | (2016.01) |
| *A23L 33/155* | (2016.01) |
| *A23K 20/163* | (2016.01) |
| *A23K 20/179* | (2016.01) |
| *A61K 8/31* | (2006.01) |
| *A61K 8/34* | (2006.01) |
| *A61K 8/60* | (2006.01) |
| *A61K 8/73* | (2006.01) |
| *A61K 9/14* | (2006.01) |
| *A61K 47/06* | (2006.01) |
| *A61K 47/10* | (2017.01) |
| *A61K 47/36* | (2006.01) |
| *A61Q 19/00* | (2006.01) |
| *A61J 3/02* | (2006.01) |
| *A61K 31/01* | (2006.01) |
| *A61K 31/047* | (2006.01) |

(52) U.S. Cl.
CPC .......... *A61K 9/1694* (2013.01); *A23K 20/163* (2016.05); *A23K 20/179* (2016.05); *A23L 5/44* (2016.08); *A23L 33/105* (2016.08); *A23L 33/155* (2016.08); *A61J 3/02* (2013.01); *A61K 8/31* (2013.01); *A61K 8/347* (2013.01); *A61K 8/60* (2013.01); *A61K 8/732* (2013.01); *A61K 9/14* (2013.01); *A61K 9/1623* (2013.01); *A61K 9/1652* (2013.01); *A61K 31/01* (2013.01); *A61K 31/015* (2013.01); *A61K 31/047* (2013.01); *A61K 31/07* (2013.01); *A61K 47/06* (2013.01); *A61K 47/10* (2013.01); *A61K 47/26* (2013.01); *A61K 47/36* (2013.01); *A61Q 19/00* (2013.01); *C07C 403/24* (2013.01); *C09B 61/00* (2013.01); *A23V 2002/00* (2013.01); *A61K 2800/42* (2013.01)

(58) Field of Classification Search
CPC ...... A23L 1/2753; A23L 1/3002; A23L 1/303; A61K 9/1623; A61K 9/1652; A61K 31/015; A61K 31/07; C07C 403/24; C09B 61/00; A23V 2002/00; A23V 2250/211; A23V 2250/5118
See application file for complete search history.

(56) References Cited

U.S. PATENT DOCUMENTS

| | | |
|---|---|---|
| 3,110,598 A | 11/1963 | Mueller et al. |
| 3,998,753 A | 12/1976 | Antoshkiw et al. |
| 4,522,743 A | 6/1985 | Horn et al. |
| 5,364,563 A | 11/1994 | Cathrein et al. |
| 6,261,598 B1 * | 7/2001 | Runge .................... A61K 31/07 424/401 |
| 7,070,812 B2 | 7/2006 | Runge et al. |
| 2003/0148099 A1 | 8/2003 | DeFreitas et al. |

FOREIGN PATENT DOCUMENTS

| | | |
|---|---|---|
| CA | 2914796 A1 | 1/1996 |
| DE | 1 211 911 A | 3/1966 |
| DE | 44 24 085 A1 | 1/1996 |
| DE | 101 04 494 A1 | 8/2002 |
| DE | 10 2004 046 026 A1 | 3/2006 |
| EP | 0 065 193 A2 | 11/1982 |

(Continued)

OTHER PUBLICATIONS

Hogan, et al., "Emulsification and microencapsulation properties of sodium caseinate/carbohydrate blends," *International Dairy Journal* (2001), vol. 11, pp. 137-144.

(Continued)

*Primary Examiner* — Lezah Roberts
(74) *Attorney, Agent, or Firm* — Drinker Biddle & Reath LLP

(57) ABSTRACT

A process for producing a preparation in powder form containing at least one carotenoid. The process contains the following steps:
i) suspending one or more carotenoids a) in an aqueous molecular dispersed or colloidal solution of at least one modified starch b) and sucrose c),
ii) comminuting the suspended particles, and
iii) subsequently converting the suspension optionally in the presence of a coating material into a dry powder;
where the suspension contains in process step ii), based on the dry matter of the aqueous suspension, from 1 to 25% by weight of at least one carotenoid, and the ratio of carotenoid a) to sucrose c) is from 1:2 to 1:80 by weight.

25 Claims, No Drawings

(56) References Cited

FOREIGN PATENT DOCUMENTS

| EP | 0 410 236 A2 | 1/1991 |
|---|---|---|
| EP | 0 937 412 A1 | 8/1999 |
| EP | 1066761 A2 | 1/2001 |
| JP | 57003861 A | 1/1982 |
| WO | WO-91/06292 A1 | 5/1991 |
| WO | WO-94/19411 A1 | 9/1994 |
| WO | WO-2006/032399 A2 | 3/2006 |

OTHER PUBLICATIONS

Inrternational Search Report for PCT/EP2006/063627, dated Oct. 17, 2006.
International Preliminary Report on Patentability for International Application PCT/EP2006/063627, dated Jan. 29, 2008.
Manz, V. U., "Die enwendund und bedeutung von synthetischen carotinoiden in der lebens- und futtermittel-sowie in der pharmazeutischen industrie", Chimia, 1967, vol. 21, pp. 329-335.
McNamee, et al., "Effect of Partial Replacement of Gum Arabic with Carbohydrates on its Microencapsulation Properties," *J. Agric. Food Chem.* (2001), vol. 49, pp. 3385-3388.

\* cited by examiner

PROCESS FOR PRODUCING A PREPARATION IN POWDER FORM CONTAINING AT LEAST ONE CAROTENOID

CROSS-REFERENCE TO RELATED APPLICATIONS

This application is a divisional application of U.S. Ser. No. 11/994,022 filed Dec. 27, 2007. U.S. Ser. No. 11/994,022 is incorporated by reference in its entirety. U.S. Ser. No. 11/994,022 is a national stage application, under 35 U.S.C. § 371, of PCT/EP2006/063627, filed Jun. 28, 2006, which claims priority of German Patent Application No. 10 2005 030 952.6, filed Jun. 30, 2005.

BACKGROUND OF THE INVENTION

The carotenoid class of substances is classified into two main groups, the carotenes and the xanthophylls. The carotenes, which are pure polyene hydrocarbons such as, for example, β-carotene or lycopene, differ from the xanthophylls which also have oxygen functionalities such as hydroxyl, epoxy and/or carbonyl groups. Typical representatives of the latter group are, inter alia, astaxanthin, canthaxanthin, lutein and zeaxanthin.

The oxygen-containing carotenoids also include citranaxanthin and ethyl β-apo-8'-carotenoate.

Oxygen-containing carotenoids are widespread in nature and occur inter alia in corn (zeaxanthin), in green beans (lutein), in paprika (capsanthin), in egg yolks (lutein) and in shrimps and salmon (astaxanthin), conferring on these foodstuffs their characteristic color.

These polyenes, which can both be obtained by synthesis and be isolated from natural sources, represent important coloring materials and active substances for the human food and animal feed industries and for the pharmaceutical sector and are, as in the case of astaxanthin, active substances with provitamin A activity in salmon.

Both carotenes and xanthophylls are insoluble in water, while the solubility in fats and oils is found to be only low, however. This limited solubility and the great sensitivity to oxidation stand in the way of direct use of the relatively coarse-particled products obtained from chemical synthesis in the coloring of human foods and animal feeds because, in coarsely crystalline form, the substances are not storage-stable and provide only poor coloring results. These effects which are disadvantageous for use of carotenoids in practice are particularly evident in an aqueous medium.

Improved color yields in the direct coloring of human foods can be achieved only by specifically produced formulations in which the active substances are in finely divided form and, if appropriate, protected from oxidation by protective colloids. In addition, use of these formulations in animal feeds leads to a greater bioavailability of the carotenoids or xanthophylls and thus indirectly to improved coloring effects, for example in egg yolk or fish pigmentation.

Various processes have been described for improving the color yields and for increasing the absorbability or bioavailability, and all of them aim at reducing the size of the crystallites of the active substances and bringing the particles to a size in the region below 10 μm.

Numerous methods, inter alia described in Chimia 21, 329 (1967), WO 91/06292 and WO 94/19411, involve the grinding of carotenoids using a colloid mill and thus achieve particle sizes of from 2 to 10 μm.

There also exist a number of combined emulsification/spray drying processes as described, for example, in DE-A-12 11 911 or in EP-A-0 410 236.

According to European patent EP-B-0 065 193, carotenoid products in finely divided powder form are produced by dissolving a carotenoid in a volatile, water-miscible organic solvent at elevated temperatures, if appropriate under elevated pressure, and precipitating the carotenoid by mixing with an aqueous solution of a protective colloid and then spray drying.

An analogous process for producing carotenoid products in finely divided powder form is described in EP-A-0 937 412 with use of water-immiscible solvents.

DE-A-44 24 085 describes the use of partially degraded soybean proteins as protective colloids for lipid-soluble active substances. The soybean proteins disclosed herein have a degree of degradation of from 0.1 to 5%.

DE-A-101 04 494 describes the production of carotenoid dry powders by use of soybean proteins together with lactose as protective colloids.

Despite the carotenoid formulations already numerously described in the prior art mentioned at the outset, there continues to be a need for improvements in these preparations, whether in relation to an increased bioavailability or, in particular, in relation to a better storage stability, for example in tablets.

BRIEF SUMMARY OF THE INVENTION

The invention relates to a process for producing a preparation in powder form containing at least one carotenoid.

It was therefore an object of the present invention to propose carotenoid-containing preparations which satisfy the abovementioned requirements.

This object has been achieved according to the invention by an aqueous carotenoid-containing suspension comprising
a) at least one carotenoid,
b) at least one modified starch and
c) sucrose,
wherein the suspension comprises, based on the dry matter of the aqueous suspension, from 1 to 25% by weight, preferably from 2 to 20% by weight, particularly preferably from 5 to 15% by weight, very particularly preferably from 8 to 13% by weight, of at least one carotenoid, and the ratio of carotenoid a) to sucrose c) is from 1:2 to 1:80, preferably from 1:3 to 1:40, particularly preferably from 1:4 to 1:18, very particularly preferably from 1:5 to 1:10, by weight.

DETAILED DESCRIPTION OF THE INVENTION

Suitable carotenoids in the context of the present invention include α- and β-carotene, lycopene, lutein, astaxanthin, zeaxanthin, capsanthin, capsorubin, α- and β-cryptoxanthin, citranaxanthin, canthaxanthin, bixin, β-apo-4-carotenal, β-apo-8-carotenal and β-apo-8-carotenoic esters or mixtures thereof. Preferred carotenoids are β-carotene, β-cryptoxanthin, lycopene, lutein, astaxanthin, zeaxanthin and canthaxanthin. Particularly preferred carotenoids are those selected from the group consisting of β-carotene, lutein, zeaxanthin and lycopene or mixtures thereof, with very particular preference for β-carotene, lycopene and lutein or mixtures thereof, especially β-carotene.

Modified starch means chemically or enzymatically produced starch transformation products. Possibilities in this connection are starch ethers, starch esters or starch phosphates. Preferred representatives of this group are starch esters, especially octenylsuccinate starch, e.g. Capsul® (sodium octenylsuccinate starch) supplied by National Starch.

The content of modified starch is, based on the dry matter of the aqueous suspension, from 5 to 50% by weight, preferably from 5 to 30% by weight, particularly preferably from 8 to 26% by weight.

A preferred embodiment of the aqueous suspension of the invention comprises at least one carotenoid as nanoparticles.

Nanoparticles mean particles having an average particle size D[4.3] determined by Fraunhofer diffraction of from 0.02 to 100 µm, preferably from 0.05 to 50 µm, particularly preferably from 0.05 to 20 µm, very particularly preferably from 0.05 to 5 µm, especially from 0.05 to 1.0 µm. The term D[4.3] refers to the volume-weighted average diameter (see handbook for Malvern Mastersizer S, Malvern Instruments Ltd., UK).

A further preferred embodiment of the aqueous suspension of the invention comprises as component d) in addition from 0.1 to 10% by weight, preferably from 0.5 to 5% by weight, particularly preferably from 0.8 to 2.5% by weight, very particularly preferably from 1 to 2% by weight, of one or more antioxidants, based on the dry matter of the aqueous suspension. Examples of suitable antioxidants include α-tocopherol, t-butyl-hydroxytoluene, t-butylhydroxyanisole, citric acid, sodium citrate, ascorbic acid, sodium ascorbate, ascorbyl palmitate or ethoxyquin or mixtures thereof. Preferred antioxidants are α-tocopherol, ascorbic acid, sodium ascorbate, ascorbyl palmitate or mixtures thereof.

To increase the stability of the active substance against microbial degradation, it may be expedient to add preservatives such as, for example, methyl-4-hydroxybenzoate, propyl 4-hydroxybenzoate, sorbic acid or benzoic acid or salts thereof to the preparation.

The aqueous suspension of the invention comprises a solids content of from 10 to 80% by weight, preferably from 30 to 75% by weight, particularly preferably from 50 to 75% by weight.

Besides the modified starch, the aqueous suspensions of the invention and the preparations in powder form produced therefrom may comprise further protective colloids. Examples of suitable substances for this purpose are the following:

bovine, porcine or fish gelatin, especially acid- or base-degraded gelatin having Bloom numbers in the range from 0 to 250, very particularly preferably gelatin A 100, A 200, A 240, B 100 and B 200, and low molecular weight, enzymatically degraded gelatin types having Bloom number 0 and molecular weights of from 15 000 to 25 000 D, such as, for example, Collagel A and Gelitasol P (from Stoess, Eberbach), and mixtures of these gelatin types.

Starch, dextrin, pectin, gum arabic, ligninsulfonates, chitosan, polystyrene sulfonate, alginates, casein, caseinate, methylcellulose, carboxymethylcellulose, hydroxypropylcellulose or mixtures of these protective colloids.

Vegetable proteins such as soybean, rice and/or wheat proteins, it being possible for these vegetable proteins to be in partially degraded or in undegraded form.

The invention also relates to a process for producing an aqueous carotenoid-containing suspension, which comprises
i) suspending one or more carotenoids a) in an aqueous molecular dispersed or colloidal solution of at least one modified starch b) and sucrose c), and
ii) comminuting the suspended particles,
where the suspension comprises after process step ii), based on the dry matter of the aqueous suspension, from 1 to 25% by weight of at least one carotenoid, and the ratio of carotenoid a) to sucrose c) is from 1:2 to 1:80 by weight.

The invention likewise relates to a process for producing an aqueous carotenoid-containing suspension, which comprises
i) suspending one or more carotenoids a) in an aqueous molecular dispersed or colloidal solution of modified starch b),
ii) comminuting the suspended particles, and
iii) mixing the fine-particle suspension with sucrose c),
where the suspension comprises after process step iii), based on the dry matter of the aqueous suspension, from 1 to 25% by weight of at least one carotenoid, and the ratio of carotenoid a) to sucrose c) is from 1:2 to 1:80 by weight.

The active substance [one or more carotenoids] is in this case suspended before the comminution, preferably in crystalline form, in the abovementioned protective colloid solution.

The comminution of the suspended particles can take place in the context of the present invention inter alia with the aid of a high-pressure homogenizer or preferably by grinding.

The grinding in process steps ii) can moreover take place in a manner known per se, e.g. using a ball mill. This entails, depending on the type of mill used, grinding until the particles have an average particle size D[4.3] determined by Fraunhofer diffraction of from 0.02 to 100 µm, preferably from 0.05 to 50 µm, particularly preferably from 0.05 to 20 µm, very particularly preferably from 0.05 to 5 µm, especially from 0.05 to 1.0 µm. The term D[4.3] refers to the volume-weighted average diameter (see handbook for Malvern Mastersizer S, Malvern Instruments Ltd., UK).

Further details on the grinding and the apparatuses used therefore are to be found inter alia in Ullmann's Encyclopedia of Industrial Chemistry, Sixth Edition, 2000, Electronic Release, Size Reduction, Chapter 3.6.: Wet Grinding, and in EP-A-0 498 824.

The degree of crystallinity of the ground carotenoid particles after the grinding process is greater than 80%, preferably greater than 90%, particularly preferably greater than 98%.

Preferred embodiments in relation to components a) to c) and the amounts thereof employed are to be found in the explanations made at the outset.

A particularly preferred embodiment of the process of the invention for producing an aqueous carotenoid-containing suspension comprises
i) suspending one or more carotenoids a) selected from the group consisting of β-carotene, lutein, zeaxanthin and lycopene or mixtures thereof in an aqueous molecular or colloidal solution of sodium octenylsuccinate starch b),
ii) grinding the suspended particles, and
iii) mixing the ground suspension with sucrose c),
where the suspension comprises after process step iii), based on the dry matter of the aqueous suspension, from 8 to 13% by weight of at least one carotenoid a) selected from the group consisting of β-carotene, lutein, zeaxanthin and lycopene or mixtures thereof, and the ratio of carotenoid a) to sucrose c) is from 1:5 to 1:10 by weight.

The invention further relates to a process for producing a preparation in powder form, comprising at least one carotenoid, which comprises
i) suspending one or more carotenoids a) in an aqueous molecular dispersed or colloidal solution of at least one modified starch b) and sucrose c),
ii) grinding the suspended particles, and
iii) subsequently converting the suspension if appropriate in the presence of a coating material into a dry powder, where the suspension comprises in process step ii), based on the dry matter of the aqueous suspension, from 1 to 25% by weight of at least one carotenoid, and the ratio of carotenoid a) to sucrose c) is from 1:2 to 1:80 by weight.

The invention additionally relates to a process for producing a preparation in powder form, comprising at least one carotenoid, which comprises
i) suspending one or more carotenoids a) in an aqueous molecular dispersed or colloidal solution of modified starch b),
ii) grinding the suspended particles,
iii) mixing the ground suspension with sucrose c), and
iv) subsequently converting the suspension if appropriate in the presence of a coating material into a dry powder,
where the suspension comprises after process step iii), based on the dry matter of the aqueous suspension, from 1 to 25% by weight of at least one carotenoid, and the ratio of carotenoid a) to sucrose c) is from 1:2 to 1:80 by weight.

Conversion into a dry powder can moreover take place inter alia by spray drying, spray cooling, modified spray drying, freeze drying or drying in a fluidized bed, if appropriate also in the presence of a coating material. Suitable coating agents include corn starch, silica or else tricalcium phosphate.

Further details of spray cooling and of modified spray drying are to be found in WO 91/06292 (pages 5 to 8).

Preferred embodiments in relation to components a) to c) and the amounts thereof employed are to be found in the explanations made at the outset.

A particularly preferred embodiment of the process of the invention for producing a carotenoid-containing preparation in powder form comprises
i) suspending one or more carotenoids a) selected from the group consisting of β-carotene, lutein, zeaxanthin and lycopene or mixtures thereof in an aqueous molecular or colloidal solution of sodium octenylsuccinate starch b),
ii) grinding the suspended particles, and
iii) mixing the ground suspension with sucrose c), and
iv) subsequently converting the suspension if appropriate in the presence of a coating material into a dry powder,
where the suspension comprises after process step iii), based on the dry matter of the aqueous suspension, from 8 to 13% by weight of at least one carotenoid a) selected from the group consisting of β-carotene, lutein, zeaxanthin and lycopene or mixtures thereof, and the ratio of carotenoid a) to sucrose c) is from 1:5 to 1:10 by weight.

The invention also relates to a preparation in powder form, comprising
a) at least one carotenoid, preferably selected from the group consisting of β-carotene, lutein, zeaxanthin and lycopene or mixtures thereof,
b) at least one modified starch, preferably from 5 to 50% by weight, particularly preferably from 5 to 30% by weight, very particularly preferably from 8 to 26% by weight, of octenylsuccinate starch and
c) sucrose,
wherein the preparation comprises, based on the total mass of the preparation in powder form, from 1 to 25% by weight, preferably from 2 to 20% by weight, particularly preferably from 5 to 15% by weight, very particularly preferably from 8 to 13% by weight, of at least one carotenoid, and the ratio of carotenoid a) to sucrose c) is from 1:2 to 1:80, preferably from 1:3 to 1:40, particularly preferably from 1:4 to 1:18, very particularly preferably from 1:5 to 1:10, by weight.

A further preferred embodiment of the preparation of the invention in powder form comprises as component d) in addition from 0.1 to 10% by weight, preferably from 0.5 to 5% by weight, particularly preferably from 0.8 to 2.5% by weight, very particularly preferably from 1 to 2% by weight, of one or more antioxidants, based on the total mass of the preparation in powder form.

Examples of suitable antioxidants include α-tocopherol, t-butyl-hydroxytoluene, t-butylhydroxyanisole, citric acid, sodium citrate, ascorbic acid, sodium ascorbate, ascorbyl palmitate or ethoxyquin or mixtures thereof. Preferred antioxidants are α-tocopherol, ascorbic acid, sodium ascorbate, ascorbyl palmitate or mixtures thereof.

The degree of crystallinity of the carotenoid particles present in the preparation in powder form—which can be determined for example by x-ray diffraction measurements—is greater than 70%, preferably in the range from 80 to 100%, particularly preferably in the range from 90 to 99%, very particularly preferably in the range from 95 to 99%.

The dry powders of the invention are notable inter alia for being redispersible without difficulty in aqueous systems to achieve a uniform fine distribution of the active substance in the particle size range below 1 μm.

Use of the inventive combination of sucrose and modified starch as formulation aids has the advantage, compared with other sugars, for example lactose or glucose, that the carotenoid formulations produced therewith show particularly high storage stability inter alia in multivitamin tablets (see table).

The carotenoid formulations of the invention are suitable inter alia as additive to human food preparations, for example for coloring human foods such as beverages, as compositions for producing pharmaceutical and cosmetic preparations, and for producing dietary supplement products, for example multivitamin products in the human and animal sector.

Implementation of the process of the invention is explained in detail in the following examples.

EXAMPLE 1

Production of a β-carotene dry powder with use of a mixture of sucrose and octenylsuccinate starch β-carotene: sucrose=1:6.6)
a.
1160 g of water were heated to 55° C. under protective gas, and 26.5 g of sodium ascorbate, 23.5 g of ascorbic acid and 500 g of octenylsuccinate starch (Capsul®, from National Starch) were added. 500 g of crystalline β-carotene were suspended in this solution by stirring. The suspension was then ground with the aid of a ball mill until the β-carotene particles had an average particle size D[4.3] measured by Fraunhofer diffraction of about 0.6 μm.
b.
2630 g of this ground suspension were transferred under protective gas into a second reactor and, while stirring, 3207 g of sucrose and a further 469 g of octenylsuccinate starch were added. The temperature of this mixture was kept at 55° C. Addition of 30 g of α-tocopherol was followed by the suspension being homogenized and subsequently being converted by modified spray drying into a dry powder in the form of beadlets. The β-carotene content in the beadlets was 11.1% and had an E1/1[1)] of 91.

EXAMPLE 2

Production of β-carotene dry powder with use of a mixture of sucrose and octenylsuccinate starch (β-carotene: sucrose=1:7.2)

1160 g of water are heated to 55° C. under protective gas, and 26.5 g of sodium ascorbate, 23.5 g of ascorbic acid and 500 g of octenylsuccinate starch (Capsul®, from National Starch) are added. 500 g of crystalline β-carotene are suspended in this solution by stirring, and the suspension is ground with the aid of a ball mill until the β-carotene particles have an average particle size D[4.3] measured by Fraunhofer diffraction of about 0.6 µm.

b.

2774 g of this ground suspension were transferred under protective gas into a second reactor and, while stirring, 3914 g of sucrose were added. The temperature of this mixture was kept at 55° C. Addition of 32 g of α-tocopherol was followed by the suspension being homogenized and subsequently converted by modified spray drying into a dry powder in the form of beadlets. The β-carotene content in the beadlets was 11.7% and had an E1/1[1)] of 89.

EXAMPLE 3

Comparative Test

Production of a β-carotene dry powder with use of a mixture of glucose syrup and octenylsuccinate starch (β-carotene:glucose syrup=1:6.6)

a.

7.5 kg of water were heated to 55° C. under protective gas, and 0.225 kg of sodium ascorbate, 0.2 kg of ascorbic acid and 4.25 kg of octenylsuccinate starch (Capsul®, from National Starch) were added. 4.25 kg of crystalline β-carotene were suspended in this solution by stirring. The suspension was then ground with the aid of a ball mill until the β-carotene particles had an average particle size D[4.3] measured by Fraunhofer diffraction of about 0.6 µm.

b.

2445 g of this ground suspension were transferred under protective gas into a second reactor and, while stirring, 3590 g of glucose syrup and a further 419.7 g of octenylsuccinate starch were added. The temperature of this mixture was kept at 55° C. Addition of 26.9 g of α-tocopherol was followed by the suspension being homogenized and subsequently converted by modified spray drying into a dry powder in the form of beadlets. The (β-carotene content in the beadlets was 10.9% and had an E1/1[1)] of 94.

EXAMPLE 4

Comparative Test

Production of a β-carotene dry powder with use of a mixture of glucose syrup and octenylsuccinate starch (β-carotene:glucose syrup=1:7.6)

2481 g of the ground suspension from Example 3a were transferred under protective gas into a second reactor and, while stirring, 4194 g of glucose syrup were added. The temperature of this mixture was kept at 55° C. Addition of 27.4 g of α-tocopherol was followed by the suspension being homogenized and subsequently converted by modified spray drying into a dry powder in the form of beadlets. The β-carotene content in the beadlets was 10.6% and had an E1/1[1)] of 96.

[1)] The E1/1 defines in this connection the specific extinction of a 1% strength aqueous dispersion of a 10% by weight dry powder in a 1 cm cuvette at the absorption maximum.

Table: Storage Stability of the β-Carotene Beadlets in Multivitamin Tablets

The stability of the β-carotene beadlets was tested by means of multivitamin mineral tablets having a content of about 3 mg of β-carotene per tablet. The tablets were packed in HDPE containers whose lid was sealed with heat-sealed aluminum foil. The tablets were stored at 40° C. and 75% relative humidity for 6 months. The β-carotene content was analyzed in each case after storage for 3 and 6 months.

TABLE

| Ex. | Sugar | BC:sugar ratio | Content: β-carotene | Initial β-carotene content per tablet [mg] | After 3 months β-carotene content per tablet [mg] | Loss (%) | After 6 months β-carotene content per tablet [mg] | Loss (%) |
|---|---|---|---|---|---|---|---|---|
| 1 | Sucrose | 1:6.6 | 11.1 | 3.66 | 3.19 | 12.8 | 3.00 | 18.0 |
| 2 | Sucrose | 1:7.2 | 11.6 | 3.86 | 3.39 | 12.2 | 3.46 | 10.4 |
| 3 | Glucose syrup | 1:6.6 | 10.9 | 3.60 | 2.67 | 25.8 | 2.75 | 23.6 |
| 4 | Glucose syrup | 1:7.6 | 10.6 | 3.40 | 2.57 | 24.4 | 2.45 | 27.9 |

We claim:

1. A process for producing a preparation in powder form, comprising at least one carotenoid, which comprises
    i) suspending one or more carotenoids in crystalline form in an aqueous molecular dispersed or colloidal solution of at least one modified starch and sucrose,
    ii) grinding the suspended particles, and
    iii) subsequently converting the suspension optionally in the presence of a coating material into a dry powder;
    where the suspension comprises in process step ii), based on the dry matter of the aqueous suspension, from 1 to 25% by weight of at least one carotenoid, and the ratio of carotenoid a) to sucrose c) is from 1:2 to 1:80 by weight and
    said at least one modified starch is present in an amount from 5 to 30% by weight, based on the dry matter of the aqueous suspension and
    wherein the ground carotenoid particles after the grinding process have a degree of crystallinity which is greater than 80%.

2. A process for producing a preparation in powder form, comprising at least one carotenoid, which comprises
    i) suspending one or more carotenoids in crystalline form in an aqueous molecular dispersed or colloidal solution of modified starch,
    ii) grinding the suspended particles,
    iii) mixing the ground suspension with sucrose, and
    iv) subsequently converting the suspension optionally in the presence of a coating material into a dry powder, where the suspension comprises after process step iii), based on the dry matter of the aqueous suspension, from 1 to 25% by weight of at least one carotenoid, and the ratio of carotenoid a) to sucrose c) is from 1:2 to 1:80 by weight and said at least one modified starch is present in an amount from 5 to 30% by weight, based on the dry matter of the aqueous suspension and wherein the ground carotenoid particles after the grinding process have a degree of crystallinity which is greater than 80%.

3. The process according to claim 1, wherein the one or more carotenoids are compounds selected from the group consisting of β-carotene, lycopene, zeaxanthin, lutein and mixtures thereof.

4. The process according to claim 2, wherein the one or more carotenoids are compounds selected from the group consisting of β-carotene, lycopene, zeaxanthin, lutein and mixtures thereof.

5. The process according to claim 3, wherein the modified starch is octenylsuccinate starch.

6. The process according to claim 4, wherein the modified starch is octenylsuccinate starch.

7. The process according to claim 2, which comprises
i) suspending one or more carotenoids in crystalline form wherein said one or more carotenoids is selected from the group consisting of β-carotene, lutein, zeaxanthin and lycopene or mixtures thereof in an aqueous molecular or colloidal solution of sodium octenylsuccinate starch,
ii) grinding the suspended particles, and
iii) mixing the ground suspension with sucrose, and
iv) subsequently converting the suspension optionally in the presence of a coating material into a dry powder,
where the suspension comprises after process step iii), based on the dry matter of the aqueous suspension, from 8 to 13% by weight of at least one carotenoid a) selected from the group consisting of β-carotene, lutein, zeaxanthin and lycopene or mixtures thereof, and the ratio of carotenoid a) to sucrose c) is from 1:5 to 1:10 by weight.

8. The process according to claim 1, wherein the one or more carotenoids are β-carotene.

9. The process according to claim 7, wherein the one or more carotenoids are β-carotene.

10. The process according to claim 1, wherein the one or more carotenoids are lycopene.

11. The process according to claim 7, wherein the one or more carotenoids are lycopene, zeaxanthin, lutein and mixtures thereof.

12. The process according to claim 1, wherein the one or more carotenoids are zeaxanthin.

13. The process according to claim 7, wherein the one or more carotenoids are zeaxanthin.

14. The process according to claim 1, wherein the one or more carotenoids are lutein.

15. The process according to claim 7, wherein the one or more carotenoids are lutein.

16. A process for producing an aqueous carotenoid-containing suspension, which comprises
i) suspending one or more carotenoids in crystalline form in an aqueous molecular dispersed or colloidal solution of at least one modified starch and sucrose, and
ii) grinding the suspended particles,
where the suspension comprises after process step ii), based on the dry matter of the aqueous suspension, from 1 to 25% by weight of at least one carotenoid, and the ratio of carotenoid a) to sucrose c) is from 1:2 to 1:80 by weight and
said at least one modified starch is present in an amount from 5 to 30% by weight, based on the dry matter of the aqueous suspension and
wherein the ground carotenoid particles after the grinding process have a degree of crystallinity which is greater than 80%.

17. The process according to claim 1, wherein said at least one modified starch is an amount from 8 to 26% by weight, based on the dry matter of the aqueous suspension.

18. The process according to claim 2, wherein said at least one modified starch is an amount from 8 to 26% by weight, based on the dry matter of the aqueous suspension.

19. The process according to claim 16, wherein said at least one modified starch is an amount from 8 to 26% by weight, based on the dry matter of the aqueous suspension.

20. The process according to claim 16, wherein the one or more carotenoids are compounds selected from the group consisting of β-carotene, lycopene, zeaxanthin, lutein and mixtures thereof and the modified starch is octenylsuccinate starch.

21. The process according to claim 7, wherein the average particle size after grinding is from 0.02 to 100 μm.

22. The process according to claim 7, wherein the average particle size after grinding is from 0.05 to 1 μm.

23. The process according to claim 7, wherein the grinding takes place using a ball mill.

24. The process according to claim 7, wherein the ground carotenoid particles after the grinding process have a degree of crystallinity which is 95 to 99%.

25. The process according to claim 7, wherein the ratio of carotenoid to sucrose of 1:5 to 1:10.

* * * * *